US007815915B2

(12) United States Patent
Wettendorff

(10) Patent No.: US 7,815,915 B2
(45) Date of Patent: *Oct. 19, 2010

(54) MIXTURE OF HUMAN PAPILLOMAVIRUS VIRUS-LIKE PARTICLES

(75) Inventor: Martine Anne Cecile Wettendorff, Rixensart (BE)

(73) Assignee: GlaxoSmithKline Biologicals, s.a., Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 12/175,874

(22) Filed: Jul. 18, 2008

(65) Prior Publication Data
US 2008/0279890 A1 Nov. 13, 2008

Related U.S. Application Data

(63) Continuation of application No. 11/746,841, filed on May 10, 2007, now Pat. No. 7,416,846, which is a continuation of application No. 10/508,222, filed as application No. PCT/EP03/002826 on Mar. 17, 2003, now Pat. No. 7,217,419.

(30) Foreign Application Priority Data
Mar. 18, 2002 (GB) ................................. 0206360.0

(51) Int. Cl.
A61K 39/12 (2006.01)
(52) U.S. Cl. ....................................... 424/204.1; 435/6
(58) Field of Classification Search ............... 424/204.1
See application file for complete search history.

(56) References Cited

U.S. PATENT DOCUMENTS

| 5,855,891 | A | 1/1999 | Lowy et al. |
|---|---|---|---|
| 6,066,324 | A | 5/2000 | Gissmann et al. |
| 6,245,568 | B1 | 6/2001 | Volkin et al. |
| 6,251,678 | B1 | 6/2001 | Volkin et al. |
| 6,908,613 | B2 | 6/2005 | Wilson et al. |
| 6,936,255 | B1 | 8/2005 | Wettendorff |
| 7,101,560 | B2* | 9/2006 | Wettendorff ............. 424/204.1 |
| 7,205,125 | B2* | 4/2007 | Castillo et al. ............. 435/69.1 |
| 7,217,419 | B2* | 5/2007 | Wettendorff ............. 424/204.1 |
| 7,279,306 | B2 | 10/2007 | Schlegel et al. |
| 7,416,846 | B2* | 8/2008 | Wettendorff ................... 435/6 |
| 2004/0121465 | A1 | 6/2004 | Robinson |
| 2004/0131638 | A1 | 7/2004 | Debrus et al. |
| 2005/0123562 | A1 | 6/2005 | Wettendorff |

FOREIGN PATENT DOCUMENTS

| EP | 689454 B1 | 9/1997 |
|---|---|---|
| WO | WO 95/17209 | 6/1995 |
| WO | WO 95/31532 | 11/1995 |
| WO | WO 96/11274 | 4/1996 |
| WO | WO 99/13056 | 3/1999 |
| WO | WO 99/45957 | 9/1999 |
| WO | WO 99/50424 | 10/1999 |
| WO | WO 00/09671 | 2/2000 |
| WO | WO 00/09699 | 2/2000 |
| WO | WO 00/23105 | 11/2000 |
| WO | WO01/17551 | 3/2001 |
| WO | WO 01/17551 | 3/2001 |
| WO | WO01/97840 | 12/2001 |
| WO | WO03/077942 | 9/2003 |
| WO | WO 2004/056389 | 7/2004 |
| WO | WO2005/032586 | 4/2005 |

OTHER PUBLICATIONS

Giuliano, et al. "Human papillomavirus infection at the United States-Mexico Border: Implications for cervical cancer prevention and control" Cancer Epidemiology Biomarkers & Prevention, 2001, 10(11), pp. 1129-1136.
Palker, et al. "Antibody, cytokine and cytotoxic T lymphocyte responses in chimpanzees immunized with human papillomavirus virus-like particles" Vaccine, Butterworth Scientific, 2001, 19(27), pp. 3733-3743.
Roden, et al. "Assesment of the serological relatedness of genital human papillomaviruses by hemagglutination inhibition" J of Virology, The American Society for Microbiology, 1996, 70(5), pp. 1996-2005.
Wheeler, "Preventive vaccines for cervical cancer" Salud Publica de Mexico, 1997, 39(4), pp. 283-287.
U.S. Appl. No. 09/807,657.
U.S. Appl. No. 10/540,099.
U.S. Appl. No. 11/477,879.
Bachtiary, et al, Impact of multiple HPV infection on response to treatment and survival in pts. receiving radical radiotherapy for cervical cancer, International Journal of Cancer, Journal International Du Cancer, US, Nov. 20, 2002, vol. 102, No. 3, pp. 237-243.
Bass, et al, Progress in the search of a vaccine against human papilloma virus, IAVI Report Oct./Nov. 2002, Online, Oct. 10, 2002, retrieved from the internet—www.aegis.com/pubs/iavi/2002/IAVI2002-1003.html, retrieved on Apr. 21, 2004.
Bosch, et al., Prevalence of human papillomavirus in cervical cancer: a worldwide perspective, J. Nat. Canc. Inst. vol. 87, No. 11, p. 796-802 (1995).
Breitburd et al., Immunization with Virus-Like Particles from Cottontail Rabbit Papillomavirus (CRPV) Can Protect Against Experimental CRPV Infection, Journal of Virology, vol. 69, p. 3959-3963(1995).
Brown, et al, A dose ranging study of the safety and immunogenicity profiles of a quadrivalent HPV (types 6, 11, 16 and 18) L1 VLP candidate vaccine in young healthy women, Abstract 0-51, 19th International Papillomavirus Conference, Sep. 2001, Florianopolis, Brazil.
Carter, et al., Comparison of human papillomavirus Types 16, 18, and 6 capsid antibody responses following incident infection, The Journal of Infectious Diseases Society of America, vol. 181, p. 19111-19119 (2000).

(Continued)

Primary Examiner—Ali R. Salimi
(74) Attorney, Agent, or Firm—Gwynedd Warren; GlaxoSmithKline - Global Patents

(57) ABSTRACT

The present invention relates to a vaccine composition comprising VLPs containing L1 proteins or functional L1 protein derivatives from HPV 16, HPV 18, HPV 31 and HPV 45 genotypes.

19 Claims, 7 Drawing Sheets

OTHER PUBLICATIONS

Chan, et al., Analysis of genomic sequences of 95 papillomavirus types: Uniting typing, phylogeny, and taxonomy, Journal of Virology, vol. 69, No. 5, pp. 3074-3083 (1995).

Chan, et al., Phylogenetic analysis of 48 papillomavirus types and 28 subtypes and variants: a showcase for the molecular evolution of DNA viruses, J. Virology, vol. 66, No. 10, p. 5714-5725 (1992).

Clifford, et al., Human papillomavirus types in invasive cervical cancer worldwide: a meta-analysis, British J. of Cancer, vol. 88, p. 63-73 (2003).

Coutlee, et al., Comparison between vaginal tampon and cervicovaginal lavage specimen collection for detection of human papillomavirus DNA by the polymerase chain reaction, Journal of Medical Virology, vol. 51, p. 42-47 (1997).

Garland, et al., An evaluation of noninferiority in antibody response to human papillomavirus (HPV) Type 16 in subjects vaccinated with monovalent (HPV 16) and quadrivalent (HPV 6, 11, 16, 18) L1 virus-like particle vaccines, published online ahead of print on Apr. 11, 2007, Clin, Vaccine Immuno. Doi:10.1128/CVI.00478-06 (2007).

Garland, et al., Noninferiority of antibody aesponse to human papillomavirus Type 16 in subjects vaccinated with monovalent and quadrivalent L1virus-like particle vaccines, Clinical and Vaccine Immunology, vol. 14, No. 6, pa 792-795 (2007).

Giroglou et al., "Immunological analyses of human papillomavirus capsids", Vaccine, vol. 19, No. 13-14, 2001, pp. 1783-1793 (2001).

Harper, Cervarix™ HPV-16/18 L1 VLP AS04 vaccine: sustained antibody levels though 5.5 years against HPV-16 and 18, presentation ESGO, Oct. 31, 2007.

Harper, et al., Sustained efficacy up to 4.5 years of a bivalent L1 virus-like particle vaccine against human papillomavirus types 16 and 18: follow-up from a randomised control trial, The Lancet, vol. 367, p. 1247-1255 (2006).

Harro, et al., Safety and immunogenicity trial in adult volunteers of a human papillomavirus 16 L1 virus-like particle vaccine, J. of the National Cancer Institute, vol. 93, No. 4, p. 284-292 (2001).

Koutsky, et al., A controlled trial of a human papillomavirus type 16 vaccine, N. Engl. J. Med., vol. 347, No. 21, p. 1645-1651 (2002).

Mach, et al., Disassembly and reassembly of yeast-derived recombinant human papillomavirus virus-like particles (HPV VLPs), J. of Pharmaceutical Sciences, vol. 95, No. 10, p. 2195-2206 (2006).

Moore, et al., Absence of canine oral papillomavirus DNA following prophylactic L1 particle-mediated immunotherapeutic delivery vaccination, Journal of General Virology 83:2299-2301,(2002).

Paavonen, et al., Efficacy of a prophylactic adjuvanted bivalent L1 virus-like-particle vaccine against infection with human papillomavirus types 16 and 18 in young women: an interim analysis of a phase III double-blind, randomised controlled trial, The Lancet, vol. 369, p. 2161-2170 (2007).

Schiller et al., Papillomavirus-like particles and HPV vaccine development, Seminars in Cancer Biology, vol. 7, No. 6, pp. 373-382 (1996).

Schiller, et al, Papillomavirus-like particle base vaccines: cervical cancer and beyond, Expert Opinion on Biological Therapy, Ashley, London, GB, vol. 1, No. 4, p. 571-581 (2001).

Shi, et al., GARDASIL®: Prophylactic human papillomavirus vaccine development—from bench top to bed-side, Clinical Pharmacology & Therapeutics, vol. 81, No. 2, p. 259-264 (2007).

Steller, et al., Cervical cancer vaccines: progress and prospects, Journal of the Society for Gynecologic Investigation, US, Sep., Oct. 2002, vol. 9, No. 5, pp. 254-264 (2002).

Suzich, et al., Systemic immunization with papillomavirus L1 protein completely prevents the development of viral mucosal papillomas, Proceedings of the National Academy of Sciences of USA, National Academy of Science, vol. 92, p. 11553-11557 (1995).

Thompson, et al., Immunogenicity & reactogenicity of a recombinant HPV6 fusion protein vaccine adjuvanted with monophosphoryl lipid A, Biochemical Society Transactions, vol. 274S p. 25 (1997).

Van Ranst, et al., Phylogenetic classification of human papillomaviruses: correlation with clinical manifestations, J. of General Virology, vol. 73, p. 2653-2660 (1992).

Villa., et al, A dose-ranging safety and immunogenicity study of a quadrivalent HPV (type 6/11/16/18) L1 VLP vaccine in women, HPV Clinical Workshop & 20th International Papillomavirus Conference 2002, Oct. 4-9, 2002, Paris, Institute Pasteur.

White, et al., "In Vitro Infection and Type-Restricted Antibody-Mediated Neutralization of Authentic Human Papillomavirus Type 16, Journal of Virology", vol. 72, No. 2, pp. 959-964 (1998).

* cited by examiner

31B165C (MIXED VLP)

39B122C (HPV 16)

MIXTURE OF HUMAN PAPILLOMAVIRUS VIRUS-LIKE PARTICLES

This application is a continuation of application Ser. No. 11/746,841, filed May 10, 2007, now U.S. Pat. No. 7,416,846, which is a continuation of application Ser. No. 10/508,222, filed Mar. 31, 2005, which is a §371 of International Application No. PCT/EP03/02826, filed Mar. 17, 2003, now U.S. Pat. No. 7,217,419, the disclosures of which are incorporated by reference herein. This application also claims benefit of the filing date of the Great Britain Application No. 0206360.0, filed Mar. 18, 2002.

The present invention relates to vaccines against HPV. In particular the invention relates to vaccines comprising virus like particles (VLPs), especially virus like particles comprising proteins from human papilloma virus (HPV).

Papillomaviruses are small DNA tumour viruses, which are highly species specific. So far, over 100 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma. Cervical cancer is the most common malignancy in developing countries, with about 500,000 new cases occurring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293-306 and Hagenesee M. E., Infections in Medicine 1997 14(7) 555-556, 559-564.

Although minor variations do occur, all HPVs genomes described have at least eight early genes, E1 to E8 and two late genes L1 and L2. In addition, an upstream regulatory region harbors the regulatory sequences which appear to control most transcriptional events of the HPV genome.

HPV L1 based vaccines are disclosed in WO94/00152, WO94/20137, WO93/02184 and WO94/05792. Such a vaccine can comprise the L1 antigen as a monomer, a capsomer or a virus like particle. Methods for the preparation of VLPs are well known in the art, and include VLP disassembly-reassembly approaches to provide enhanced homogeneity, for example as described in WO9913056 and U.S. Pat. No. 6,245,568. Such particles may additionally comprise L2 proteins. L2 based vaccines are described, for example, in WO93/00436. Other HPV vaccines are based on the Early proteins, such as E7 or fusion proteins such as L2-E7.

Despite the work on HPV vaccines there is still no broadly effective vaccine against cervical cancer.

The present invention relates to an improved vaccine against human papilloma virus.

In a first aspect the present invention relates to a vaccine composition comprising VLPs containing L1 proteins or functional L1 protein derivatives from HPV 16, HPV 18, HPV 31 and HPV 45.

The invention also relates to a method of vaccine production, the method comprising combining VLPs containing L1 proteins or functional L1 protein derivatives from HPV 16, HPV 18, HPV 31 and HPV 45.

The invention further relates to use of a mixture of VLPs containing L1 proteins or functional L1 protein derivatives from HPV 16, HPV 18, HPV 31 and HPV 45 in the preparation of a vaccine for the prevention of cervical cancer.

The invention further relates to a method of preventing cervical cancer, the method comprising delivering to an individual at risk of cervical cancer an effective amount of a vaccine as described above, such as a vaccine comprising a mixture of HPV 16, HPV 18, HPV31 and HPV 45 VLPs.

The VLPs of the present invention can be formed from either the full length HPV L1 protein or certain L1 derivatives using standard methods in the art, for example as disclosed in WO99/13056 incorporated herein by reference.

It is preferred that the L1 protein used to form the VLP is a truncated L1 protein. Preferably at least one of the VLPs comprises a truncated L1 protein, and preferably all the L1 proteins in the combination vaccine are truncated L1 proteins. Preferably the truncation removes a nuclear localisation signal. Preferably the truncation is a C-terminal truncation. Preferably the C-terminal truncation removes fewer than 50 amino acids, more preferably fewer than 40 amino acids. Most preferably the C terminal truncation removes 34 amino acids from HPV 16 and 35 amino acids from HPV 18.

Truncated L1 proteins are suitably functional L1 protein derivatives. Functional L1 protein derivatives are capable of raising an immune response (if necessary, when suitably adjuvanted), said immune response being capable of recognising a VLP consisting of the full length L1 protein and/or the HPV type from which the L1 protein was derived.

VLPs of the invention may also comprise other types of functional protein derivatives, including mutants of the full length or truncated HPV L1 proteins such as deletion, substitution, or insertion mutants. Suitable derivatives also include codon optimised sequences. The L1 protein or derivative may also be a fusion protein, such as the fusion of the L1 protein with L2 or an early protein. Preferably fusion proteins comprise proteins from only one HPV genotype. VLPs made from chimaeric L1 proteins in which L1 proteins from one genotype are linked to L1 proteins from other genotypes are not preferred.

The L1 protein or functional protein derivative is suitably able to form a VLP, and VLP formation can be assessed by standard techniques such as, for example, electron microscopy and dynamic laser light scattering.

Preferably the polydispersity of the VLPs is less than 0.15, most preferably less than 0.1 and more preferably less than 0.08 when measured using a Malvern Zetasizer 3000HS under conditions as described herein.

Use of the term 'protein' or reference to a specific protein e.g. 'L1' is hereinafter taken to include reference to functional protein derivatives, unless otherwise indicated or obviously apparent from the context.

In a preferred aspect of the invention the vaccine of the invention has only four VLP types —HPV 16, HPV 18, HPV 31 and HPV 45 VLPs. Preferably the VLPs are L1-only VLPs from each of these 4 genotypes.

Alternatively, and most preferred, the vaccine comprises an additional HPV valency, making a pentavalent vaccine. Preferably the additional valency is a VLP comprising an L1 protein or functional derivative, as above, from one of HPV 52, 53, 58, 33, 35, 56, and 59. Preferably the $5^{th}$ genotype is HPV 33 when the vaccine is for use in South America or HPV 52, 53 or 58 when the vaccine is for use in Asia.

The present invention also extends to vaccines comprising 2 or more additional valencies, to provide a vaccine with 6 or more genotypes.

In one preferred embodiment the combination excludes VLPs from HPV 6a, 6b or HPV 11 genotypes.

Preferably the vaccine of the invention is at least 55% effective in preventing cervical cancer, more preferably 60%, 65%, 70%, 75% preferably 80% or even more effective in prevention of cervical cancer. For the avoidance of doubt, % efficacy in prevention of cervical cancer means protection against all cervical cancer induced by HPV infection, and not just protection against cancer caused by one genotype. Prevention may be suitably assessed over 1 year post initial vaccination, although preferred vaccines are equally effective over 2, 3, 4, 5 or more years. The % efficacy can be increased by selecting appropriate HPV genotypes to target the vaccine formulation to specific geographical areas.

Preferably the combination of VLPs within the vaccine does not reduce the immunogenicity of each VLP type. In particular it is preferred that there is no interference between HPV VLPs in the combination of the invention, such that the combined VLP vaccine of the invention is able to offer effective protection against infection by each HPV genotype represented in the vaccine. Suitably the immune response against a given VLP type in the combination is at least 50% of the immune response of that same VLP type when measured individually, preferably 100% or substantially 100%. For responses to the HPV 16 and HPV 18 VLPs, the combined vaccine of the invention preferably stimulates an immune response which is at least 50% of that provided by a combined HPV 16/HPV 18 VLP vaccine. Suitably the immune response generated by the vaccine of the invention is at a level in which the protective effect of each VLP type is still seen. The immune response may suitably be measured, for example, by antibody responses, as illustrated herein.

The vaccine of the invention may be used to treat or prevent HPV infection and/or disease. For example the vaccine may be used therapeutically to reduce viral load and/or infections that lead to cervical carcinoma or CIN III sequelae. The invention thus relates to use of the vaccine of the invention in the therapeutic treatment of diseases related to HPV infection and in prophylaxis of infection or disease. The invention also relates to use of the VLP combination of the invention in generation of an immune response against HPV 16, 18, 31 and 45.

The vaccine of the invention may optionally be formulated with VLPs which provide protection against genital warts, such as VLPs containing L1 protein from HPV 6a, 6b and/or HPV 11 genotypes.

Preferably the VLPs comprise the HPV L1 protein only and no L2 protein or protein fragment.

Vaccines of the invention may comprise other proteins or protein fragments in addition to the L1 protein or derivative. Proteins/peptides may be delivered in chimaeric form with the L1 protein in the VLP, encapsulated within a VLP or co-formulated in a mixture with the VLP's. Other proteins or peptides may also be co-administered with the vaccine of the invention.

In one aspect the vaccine comprises an HPV L2 protein or L2 derivative such as an L2 peptide, for example as disclosed in K. Kawana et al Vaccine 19, (2001) p 1496-1502, incorporated herein by reference. In a further preferred embodiment the vaccine of the invention may be formulated with HPV early antigens such as E1, E2, E3, E4, E5, E6, E7, E8 or immunologically active derivatives thereof. When delivered in chimaeric form it is preferable to utilise an immunogenic fragment of about 30-60 amino acids of the early antigen.

Optionally the vaccine may also be formulated or co-administered with non-HPV antigens. Suitably these antigens can provide protection against other diseases, most preferably sexually transmitted diseases such as herpes simplex virus, chlamydia and HIV. We particularly prefer that the vaccine comprises gD or a truncate thereof from HSV, preferably the gD2t protein as described in WO 99/45957. In this way the vaccine provides protection against both HPV and HSV. Preferred HIV antigens are described in WO/9916884 and WO/0154719.

The present invention generally relates to a mixture of VLPs containing capsid proteins from HPV 16, 18, 31 and 45, such as L1-only VLPs.

In a particularly preferred embodiment, the invention provides a vaccine comprising a mixture of HPV 16 VLPs, HPV 18 VLPs, HPV 31 VLPs and HPV 45 VLPs. Reference herein to 'HPV 16 VLP', for example, is a reference to an L1 VLP wherein the L1 protein or L1 derivative is from HPV 16. The same nomenclature principle applies, by extension, to other VLPs described herein, such as HPV 18, HPV 31 and HPV 45 VLPs.

Preferably each VLP contains L1 protein from only 1 HPV genotype. Such a vaccine may be formulated by production of individual VLPs from HPV 16, 18, 31 and 45, followed by combination of such VLPs. Preferably there are no other HPV proteins in the VLP other than L1.

Also preferred are VLPs containing proteins from only one HPV genotype, such as VLPs with L1 and L2 from HPV 16.

However, in an alternative embodiment of the invention, the VLPs may be mixed VLPs, a mixed VLP comprising L1 protein from one genotype in combination with L1 protein from a second genotype, wherein the different L1 proteins are not chimaeric L1 proteins, but associate together within the same capsid structure to form immunogenic VLPs.

Preferred combinations include any permutation of genotypes 16, 18, 31 and 45—for example, the invention may comprise a mixed HPV 16/HPV 18 VLP in combination with a mixed HPV31/HPV 45 VLP, or mixed 16/31 VLPS in combination with mixed 18/45 VLPs. Combinations of more than 2 L1 genotypes within 1 VLP are also contemplated.

Mixed VLPs may be produced by separate expression of the individual L1 proteins followed by combination to form VLPs, as exemplified herein. Alternatively multiple L1 proteins may be expressed within the same cell, from one or more DNA constructs. For example, multiple DNA constructs may be transformed or transfected into host cells, each vector encoding a different L1 protein. Alternatively a single vector having multiple L1 genes, controlled by a shared promoter or multiple individual promoters, may be used. IRES elements may also be incorporated into the vector, where appropriate. Using such expression strategies the co-expressed L1 proteins may be co-purified for subsequent VLP formation, or may spontaneously form mixed VLPs which can then be purified.

Where mixed VLPs are used, a preferred process for mixed VLP production comprises preparation of VLP L1 proteins or derivatives, such as L1 proteins, from different papillomavirus genotypes, mixing the proteins if necessary and assembly of the proteins to produce mixed VLPs. The L1 proteins may be in the form of a crude extract, be partially purified or purified prior to mixing. Preferably the proteins are at least partially purified before being combined. Optionally, further purification of the mixed VLPs may be carried out after assembly. Where additional antigens are used, then these may be added where appropriate.

In one embodiment mixed VLPs may be made by disassembly of 2 or more VLPs, followed by combination of the disassembled VLP components at any suitable point prior to reassembly. This approach is suitable when VLPs spontaneously form when the L1 protein is expressed, as occurs for example, in some yeast strains. Where the expression of the L1 protein does not lead to spontaneous VLP formation, preparations of L1 proteins or capsomers may be combined before assembly into VLPs.

Assembly of VLPs is generally achieved by removal of a reducing agent. As such, in mixed VLP production, the mixing of proteins preferably takes place prior to the removal of a reducing agent from the mixture of proteins. Preferably the production of mixed VLPs comprises the step of mixed VLP formation from a mixture of dissociated L1 proteins by removal of a reducing agent from the mixture under conditions that allow VLPs to form.

Preferably the reassembly process results from removal of a reducing agent such as β-mercaptoethanol.

It is, however, known that VLP formation is dependent upon pH, metal ions and salinity as well as the presence of a reducing agent. As such, under certain circumstances, it may be envisaged that VLPs might form in the presence of a reducing agent. It is only important to the invention that mixing of the proteins from different genotypes occurs prior to the change in environmental condition that allows the mixed VLPs to form, whether this is pH, metal ions, salinity, reducing environment or combination of these.

Where mixed VLPs are used, preferably the components of the VLPs are mixed in the proportions in which they are desired in the final mixed VLP. For example, a mixture of the same amount of a partially purified L1 protein from HPV 16 and HPV 18 provides a mixed VLP with approximately equal amounts of each protein.

Vaccine solutions comprising mixed VLPs may be stabilised by compositions known in the art, such as those of WO 98/44944, WO0045841, incorporated herein by reference.

For all vaccines of the invention, it is preferred that the vaccine is used for the vaccination of adolescent girls aged 10-15, preferably 10-13 years. The vaccine may also be administered to women following an abnormal pap smear or after surgery following removal of a lesion caused by HPV.

Preferably the vaccine is delivered in a 2 or 3 dose regime, for example in a 0, 1 month regime or 0,1 and 6 month regime respectively. Suitably the vaccination regime incorporates a booster injection after 5 to 10 years, preferably 10 years.

Preferably the vaccine is a liquid vaccine formulation, although the vaccine may be lyophilised and reconstituted prior to administration.

The vaccines of the invention may also comprise adjuvants in combination with the VLPs. Suitably the VLPs of the invention are used in combination with aluminium, and are suitably adsorbed or partially adsorbed onto aluminium adjuvants. Also preferred are adjuvants which stimulate a Th1 type response such as 3DMPL or QS21. Suitably the adjuvant is an aluminium salt, preferably in combination with 3D MPL, such as aluminium phosphate and 3D-MPL.

A preferred adjuvant is aluminium hydroxide, with the combination of aluminium hydroxide with 3D-MPL especially preferred.

When VLPs are adsorbed on to aluminium containing adjuvants, the adjuvant is preferably added before mixing of the VLPs to form the final vaccine product.

The vaccine may also comprise aluminium or an aluminium compound as a stabiliser, and the present invention also relates to a stabilised combination vaccine wherein the VLPs are adsorbed onto an aluminium salt. Suitably the VLPs are more stable over time after adsorption onto an aluminium salt than in the absence of aluminium. Preferably stabilised VLPs are obtained or obtainable by methods according to example 1 section C3.

The vaccines of the invention may be provided by any of a variety of routes such as oral, topical, subcutaneous, musosal (typically intravaginal), intraveneous, intramuscular, intranasal, sublingual, intradermal and via suppository. Intramuscular and intradermal delivery are preferred.

The dosage of VLP and other proteins will vary with the condition, sex, age and weight of the individual, the administration route and HPV of the vaccine. The quantity may also be varied with the number of VLP types. Suitably the delivery is of an amount of VLP suitable to generate an immunologically protective response. Suitably each vaccine dose comprises 1-100 μg of each VLP, preferably 5-80 μg, more preferably 5-30 μg each VLP, most preferably 5-20 μg of each VLP with 5 μg, 6 μg, 10 g, 15 μg or 20 μg especially preferred.

The multivalent vaccine of the present invention is suitably produced by combining purified L1 VLPs. Methods for the production of L1 VLPs are well known in the art, and include for example methods given in WO9531532, WO9615247, WO00/09671 and U.S. Pat. No. 5,888,526, the whole contents of which are incorporated herein.

Suitably the VLPs of the invention are made by disassembly and reassembly of VLPs, to provide homogenous and pure VLPs. Examples of suitable processes are given in WO0057906, U.S. Pat. No. 6,245,568 and WO9913056.

Preferably the VLPs are prepared from insect cells such as Sf9 or Hi-5 cells, although any suitable cells such as *E. coli* or yeast cells, for example, *S. cerevisiae S. pombe* or *Pichia* sp. may also be used.

Preferably the purification of VLPs after L1 expression includes one or more of the steps of anion exchange chromatography (Di methyl amino ethyl—DMAE), anion exchange chromatography (trimethyl amino ethyl—TMAE), hydroxyapatite chromatography, filtration such as nanometric filtration or ultrafiltration, or hydrophobic interaction chromatography. Preferably at least one anion exchange step is performed during purification, and more preferably 2 anion exchange steps are used. Preferably at least one anion exchange purification step is performed prior to mixing the proteins. Optionally a UV irradiation step may be employed.

For the avoidance of doubt, the entire teaching of all documents referred to herein is incorporated by reference.

The present invention is illustrated by the following non-limiting Examples and Figures, wherein.

EXAMPLE 1

Figure 1:
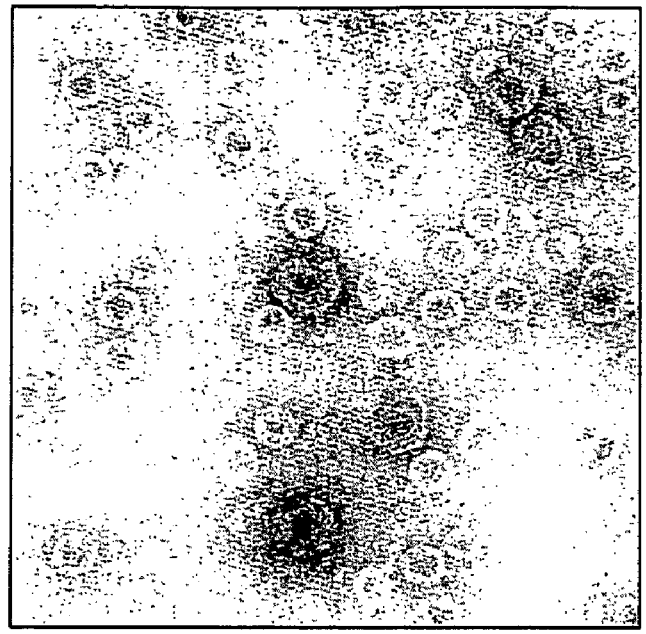
FIG. 1 illustrates mixed VLPs in comparison with HPV 16 VLPs as assessed by EM.
Figure 1:
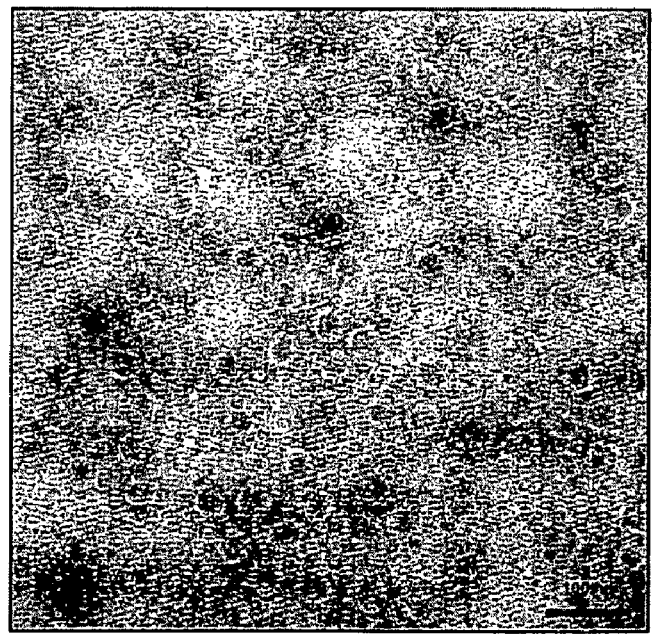

The combination of HPV 16 and HPV 18 L1 VLPs is detailed herein. L1 proteins from other HPV genotypes may be readily produced by similar methods, already known in the art.

A Preparation of HPV 16/18 L1 VLPs

Production of HPV 16 and HPV 18 VLPs was carried out using standard protocols—for example, see WO9913056.

HPV 16/18 proteins were expressed in *Trichoplusia ni* (High Five™) cells (at a density of ~350000 cells/ml) infected with recombinant Baculovirus (MOI of 0.3) encoding the HPV 16 or 18 L1 gene of interest. Cells were harvested approximately 72 hours post infection.

B Cell Harvest/Antigen Extraction

The antigen (L1-16/18) was extracted from Hi5 cells in a three step process of concentration, extraction, clarification. The concentration step consists removes up to 90% of the culture medium, and was performed by tangential flow filtration. The extraction step was performed with a hypotonic buffer (Tris 20 mM, pH 8.5). A volume equal to the culture volume was used to perform the extraction. A contact time of minimum half an hour under smooth agitation was used. The clarification was performed by tangential flow filtration.

C Purification

The purification process was carried out at room temperature. β-mercaptoethanol (4% w/w) was added to the extract in order to disassemble the VLP's into capsomers, for both antigens, L1-16/18. Glycerol was added up to a concentration of w/w 10% just prior to the addition of β-mercaptoethanol.

All buffers used were filtered on 0.22 μm filters prior to storage at 2° C.-8° C. Prior to each purification run, gel matrixes are sanitised and equilibrated with appropriate buffer before sample loading.

Purification regiemes are given for the separate purification of L1 from both HPV 16 and 18. These schemes are broadly similar, and involve the steps of:

Anion exchange chromatography (Di methyl amino ethyl—DMAE),
Anion exchange chromatography (trimethyl amino ethyl—TMAE),
Hydroxyapatite chromatography,
Nanometric filtration (Planova),
Ultrafiltration,
Hydrophobic interaction chromatography (using Octyl Sepharose) for HPV 18 or Anion exchange chromatography (DEAE) for HPV 16; and
Sterile filtration.

Specifically:

C1 Purification of L1-18 Antigen

Anion Exchange Chromatography DMAE

The clarified extract (protein at a concentration of ~1 g/ml, with the L1 protein at ~150 mg/ml) is applied to an anion exchange column (Di Methyl Amino Ethyl). Elution is performed with (Tris 20 mM|NaCl 200 mM|4% β-mercaptoethanol BME) buffer, pH 7.9±0.2. The antigen is eluted in approximately 5 column volumes and the elution profile is monitored at 280 nm.

Anion Exchange Chromatography TMAE

The eluate of the first step is diluted with 1 volume of $H_2O$/BME 4%. The diluted eluate is then applied to a second anion exchange column (Tri Methyl Amino Ethyl). Elution is performed with (20 mM Tris|NaCl 200 mM|4% BME) buffer, pH 7.9±0.2. The antigen is eluted in approximately 4 column volumes and the elution profile is monitored at 280 nm.

Hydroxyapatite Chromatography

The eluate of the TMAE step is applied to a hydroxyapatite (HA) column. After sample application, the gel is eluted with approximately 2.5 column volumes of ($NaH_2PO_4$ 100 mM|NaCl 30 mM|4% BME) buffer, pH 6.0±0.2.

Nanometric Filtration (Planova)

The HA eluate is diluted in order to reach the following conditions: ($NaH_2PO_4$ 25 mM|NaCl 10 mM|4% BME) buffer, pH 7.5±0.2.

Then it is filtered successively on a 0.2 μm prefilter and on a Planova 15N filter of 0.12 $m^2$. The filtration is performed at constant pressure 200 mbar±20 mbar.

Ultrafiltration

The ultrafiltration is performed with a tangential flow ultrafiltration system equipped with polyethersulfone membranes (Centramate cassette 0.1 $m^2$, 100 kD).

The Planova eluate is treated to reach the following conditions: ($NaH_2PO_4$ 100 M|NaCl 30 mM|4% BME), pH 6.0±0.2; then it is loaded in the system, concentrated 5 fold and dia-filtrated with continuous injection of ~10 starting volumes of ($NaH_2PO_4$ 20 mM|NaCl 500 mM) buffer, pH 6.0±0.2.

Hydrophobic Interaction Chromatography (Octyl Sepharose)

The ultrafiltration permeate is applied to an Octyl Sepharose column.

This chromatography step is run in the negative mode with approximately 5 column volumes of ($Na_3PO_4$ 20 mM|NaCl 500 mM) buffer, pH 6.0±0.2.

Sterile Filtration

The purified L1-18 antigen solution is sterilised by filtration on a 0.22 μm membrane.

C2 Purification of L1-16 Antigen

Anion Exchange Chromatography DMAE

The clarified extract is applied to an anion exchange column (Di Methyl Amino Ethyl).

Elution is performed with (Tris 20 mM|NaCl 180 mM|4% BME) buffer, pH 7.9±0.2. The antigen is eluted in approximately 4 column volumes and the elution profile is monitored at 280 nm.

Anion Exchange Chromatography TMAE

The eluate of the first step is diluted with 1 volume of $H_2O$/BME 4%. The diluted eluate is then applied to a second anion exchange column (Tri Methyl Amino Ethyl). Elution is performed with (20 mM Tris|NaCl 180 mM|4% BME) buffer, pH 7.9±0.2. The antigen is eluted in approximately 5 column volumes and the elution profile is monitored at 280 nm.

Hydroxyapatite Chromatography (HA)

The eluate of the TMAE step is applied to a HA column.

After sample application, the gel is eluted with approximately 3 column volumes of ($NaH_2PO_4$ 100 mM|NaCl 30 mM|4% BME) buffer, pH 6.0±0.2.

Nanometric Filtration (Planova)

The HA eluate is diluted in order to reach the following conditions: ($NaH_2PO_4$ 25 mM|NaCl 10 mM|4% BME) buffer, pH 7.5±0.2.

Then it is filtered successively on a 0.2 μm prefilter and on a Planova 15N filter of 0.12 $m^2$. The filtration is performed at constant pressure 200 mbar±20 mbar.

Ultrafiltration

The ultrafiltration is performed with a tangential flow ultrafiltration system equipped with polyethersulfone membranes (Centramate cassette 0.1 $m^2$, 100 kD).

The Planova eluate is treated to reach the following conditions: ($NaH_2PO_4$ 100mM|NaCl 30 mM|4% BME), pH 6.0±0.2; then it is loaded in the system, concentrated 5 fold and dia-filtrated with continuous injection of ~10 starting volumes of (NaH$_2$PO$_4$ 20 mM|NaCl 500 mM) buffer, pH 6.0±0.2.

Anion Exchange Chromatography DEAE

The ultrafiltration eluate is adjusted to the conductivity of the equilibrium buffer, (Na$_3$PO$_4$ 20 mM|NaCl 250 mM), pH 6.0±0.2 and applied on an anion exchange column (Di Ethyl Amino Ethyl).

Elution is performed with (NaH$_2$PO$_4$ 20 mM|NaCl 500 mM) buffer, pH 6.0±0.2. The antigen is eluted in approximately 3 column volumes and the elution profile is monitored at 280 nm.

Sterile Filtration

The purified L1-16 antigen solution is sterilised by filtration on a 0.22 μm membrane.

C3

Each VLP type is adsorbed independently to produce a concentrated adsorbed monovalent.

Preparation of VLP 16 Concentrated Adsorbed Monovalent:

60 μg of purified VLPs from HPV16 are adsorbed on 150 μg Al$^{3+}$ from Al(OH)$_3$, at a pH of 6.0±0.2, for one hour at room temperature with gentle stirring. This concentrated adsorbed monovalent is stored at +4° C. Adsorption is checked by centrifuging the preparation and quantifying VLPs in the supernatant.

Preparation of VLP18 Concentrated Adsorbed Monovalent:

60 μg of purified VLPs from HPV18 are adsorbed on 150 μg Al$^{3-}$ from Al(OH)$_3$, at a pH of 6.0±0.2, for one hour at room temperature with gentle stirring. This concentrated adsorbed monovalent is stored at +4° C. Adsorption is checked by centrifuging the preparation and quantifying VLPs in the supernatant.

D Final Vaccine Preparation:

Concentrated adsorbed monovalents prepared by the above method were combined to form a suspension containing 20 μg each VLP per dose. Final vaccine is stored at +4° C.

Addition of VLPs from HPV 31 and 45 at a concentration of 20 μg each VLP completes the tetravalent vaccine.

The combined adsorbed bulks, or individual adsorbed bulks, may be further mixed with adjuvants such as 3D-MPL.

EXAMPLE 2

A Preparation of HPV 16/18 L1 VLPs

Production of HPV 16 and HPV 18 VLPs was carried out using standard protocols—as above B Formation of Mixed VLPs The process of the invention involves disassembly and then reassembly of the HPV 16 and 18 VLPs such that the reassembly of HPV L1 16 and 18 is carried out together to permit the formation of a mixed VLP.

The HPV 16 and 18 VLPs may be combined at any suitable point in the above process prior to the point at which the VLPs are reassembled.

By way of example 2 specific strategies have been tested:
1 mixing of both antigens after the HA step. Based on the L1 concentration in HA pools, the two components are mixed to reach an equal concentration of HPV16 and 18 to start the UF step. In this case after the ultrafiltration step an Octyl speharose step is performed as for HPV 18 purification followed by a DEAE step as performed in the HPV 16 procedure.
2 mixing of both extracts and copurify. Based on the L1 concentration in Extracts, the two valences are mixed to reach an equal concentration of HPV16 and 18 to start the DMAE step. Again, after the ultrafiltration step an Octyl speharose step is performed as for HPV 18 followed by a DEAE step as performed in the HPV 16 procedure.

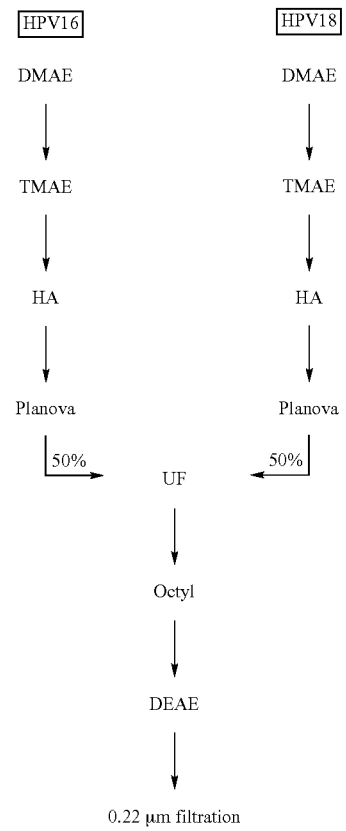

HPV16-HPV18 VLP-Mixed at DMAE Step

The same flow sheet is applied but the mixing is performed at the DMAE step instead of the UF step. The concentration used for elution at the anion exchange DMAE TMAE steps is 200 mM.

Results

HPV16-HPV18 VLP-Mixed at UF Step 2 lots of mixed VLPs (lot numbers 31b165c and 31b166c) were produced by combining HPV 16 and HPV 18 L1 proteins.

Purity by SDS-Page

The purity of the mixed VLP's was as good as both "classical" HPV 16 or HPV 18 bulks. The purity of the bulks was higher than 95%.

EM Data—FIG. 1

The EM of 31B165C (UF Retentate after maturation) was compared to a classical HPV16 lot (39B122c). VLP's were well formed, homogeneous in size, without aggregation; some ribbons of capsomeres are present in both experiments.

Size Distribution

The size distribution of the VLP's were determined using a Malvern Zetasizer 3000 HS.

The samples were measured undiluted into a plastic cuvette for Malvern analysis (800 µl/cuvette).

The technical conditions were:
laser wavelength: 532 nm,
laser power: 50 mW,
scattered light detected at 90°,
temperature: 25° C.,
duration: automatic determination by the software,
number: 3 consecutive measurements,
z-average diameter: by cumulants analysis,
size distribution: by the Contin method.

Classical results for HPV18 L1-VLP's are: 70-80 nm with good polydispersity (<0.1)

Classical results for HPV16 L1-VLP's are: 60-70 nm with good polydispersity (<0.1)

For mixed VLP's, the following results were obtained:

31 B165c: 85 nm with good polydispersity (0.08). VLP's are almost completely formed at the beginning of maturation 31 B166c: 76 nm with good polydispersity (0.08).

Figure 2:
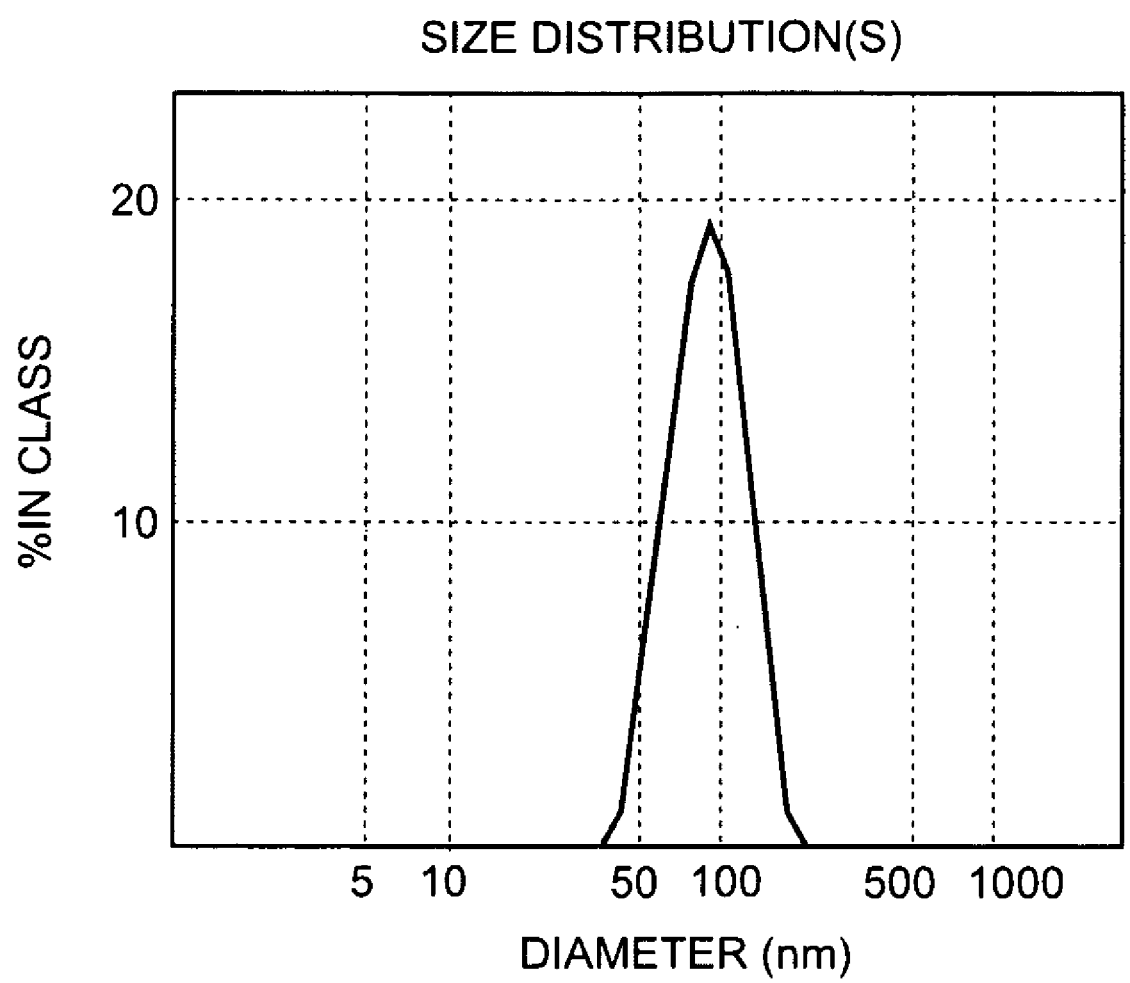
FIGS. 2 and 3 illustrate size distribution of mixed VLPs.
Figure 3:
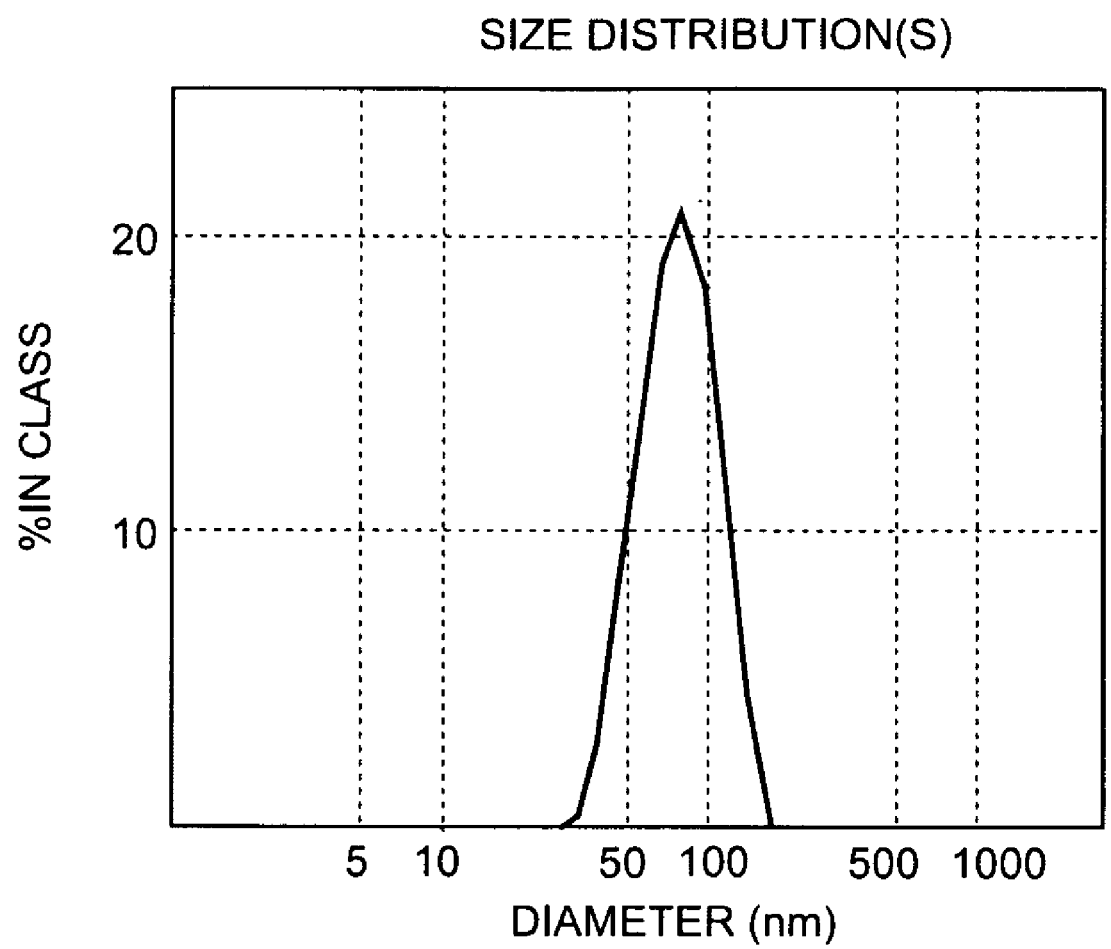
Figure 4:
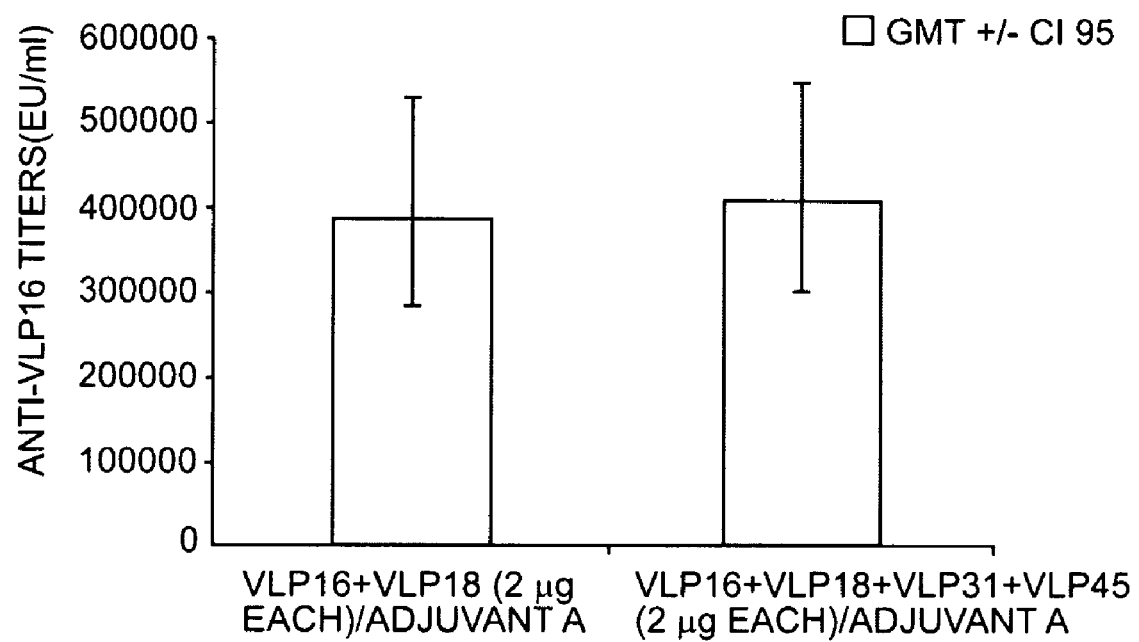
FIG. 4 illustrates antibody responses against VLP 16 in a mixed HPV 16, 18, 31, 45 combination vaccine vs. an HPV 16 control.
Figure 5:
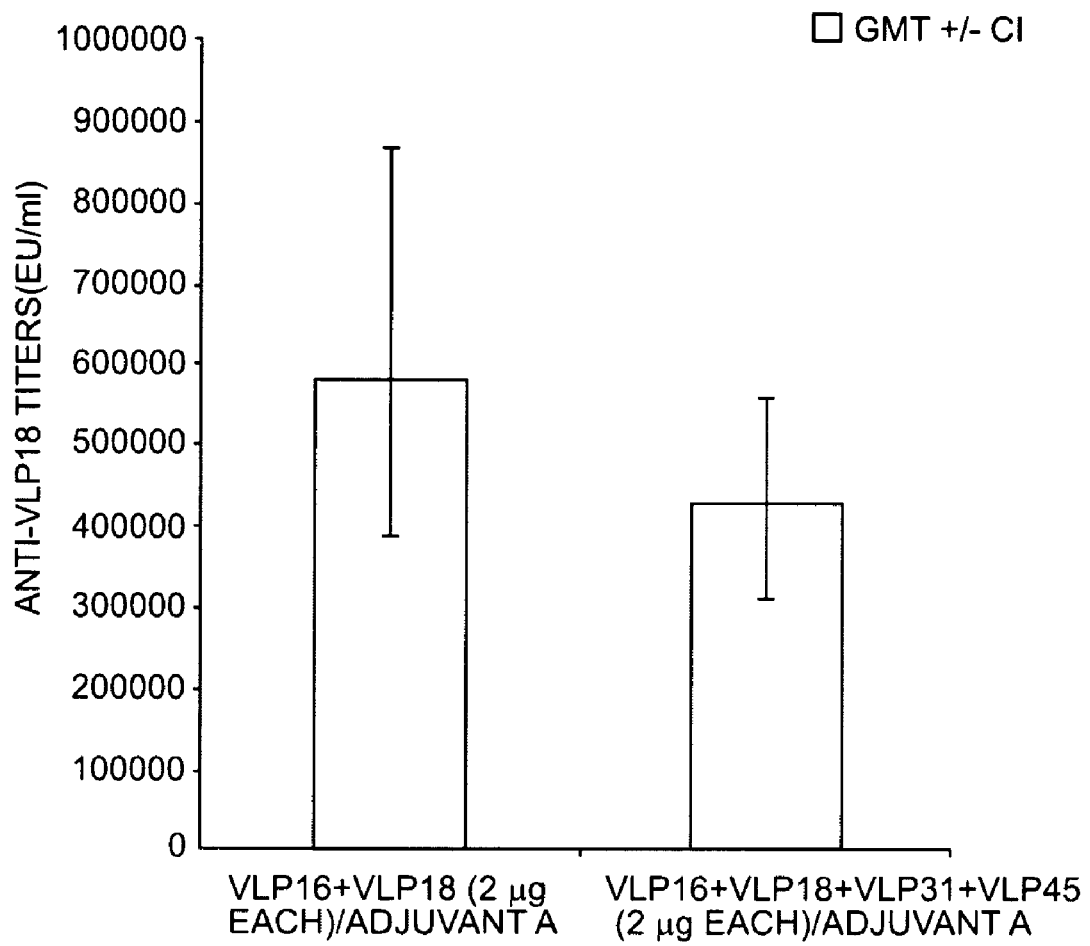
FIG. 5 illustrates antibody responses against VLP 18 in a mixed HPV 16, 18, 31, 45 combination vaccine vs. an HPV 18 control.
Figure 6:
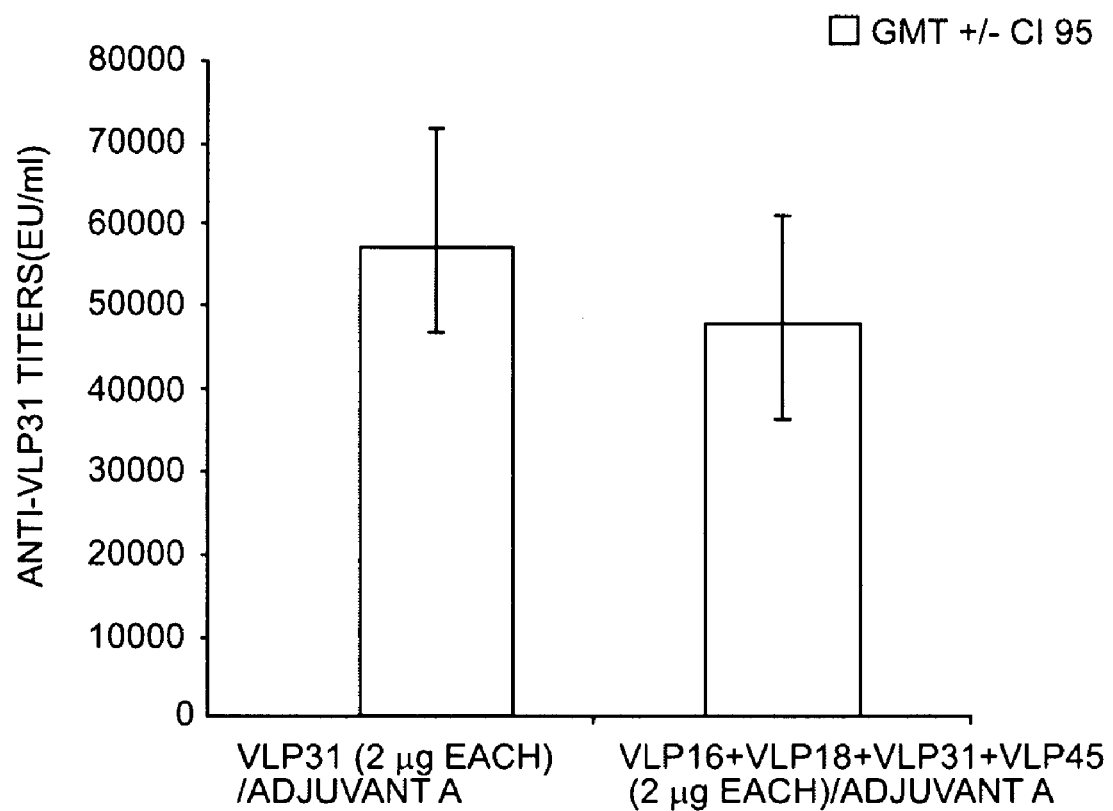
FIG. 6 illustrates antibody responses against VLP 31 in a mixed HPV 16, 18, 31, 45 combination vaccine vs. an HPV 31 control.
Figure 7:
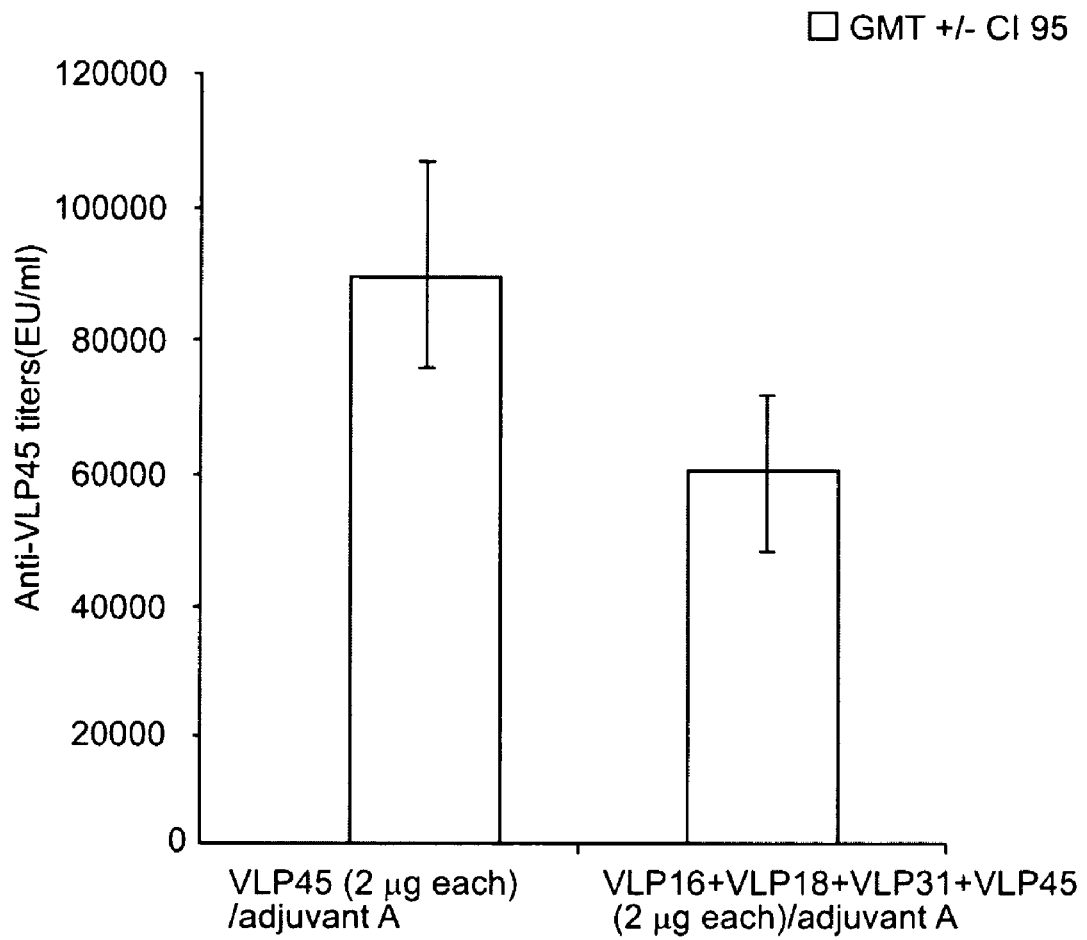
FIG. 7 illustrates antibody responses against VLP 45 in a mixed HPV 16, 18, 31, 45 combination vaccine vs. an HPV 45 control.

The size distribution of lot 31 B165c and 31 B 166c as measured by dynamic laser light scattering is shown in FIGS. 2 and 3.

HPV16-HPV18 VLP Mixed at DMAE Step

Lot n°. 31B167B was made up from lots E18L1C005 (HPV18) and 39B167 (HPV16).

Purity by SDS-Page

The purity of the mixed VLP's was as good as both "classical" bulks.

The purity of the bulks was higher than 95%.

Size Distribution

The size distribution of the VLP's were determined by using a Malvern Zetasizer 3000 HS.

Classical results for HPV18 L1-VLP's are: 70-80 nm with good polydispersity (<0.1)

Classical results for HPV16 L1-VLP's are: 60-70 nm with good polydispersity (<0.1)

For mixed VLP's, the following results were obtained:

HPV16-HPV18 31B167B: 74 nm with good polydispersity (0.07). VLP's were almost completely formed at the beginning of maturation

EXAMPLE 3

Production of a Mixed HPV 16, 18, 31, 45 Combination Vaccine

Introduction

An immunogenicity study was performed in Balb/C mice using a combination of C-terminally truncated L1 VLPs 16, 18, 31 & 45 adjuvanted with alum+3D-MPL (herein 'adjuvant A'—50 µg aluminium salt and 5 µg 3D MPL)

4 groups of 10 mice were immunised twice intramuscularly on day 0 and 21 respectively with:
1. VLP 31 (2 µg)/adjuvant A
2. VLP 45 (2 µg)/adjuvant A
3. VLP 16 (2 µg) and VLP 18 (2 µg)/adjuvant A
4. VLP 16 (2 µg), VLP 18 (2 µg), VLP 31 (2 µg), VLP 45 (2 µg)/adjuvant A Antibody responses against VLPs 16, 18, 31 and 45 were monitored on sera taken at day 35 (14 days post dose II).

Results are shown in FIGS. 4-7

Antibody Response Against VLP 16

Strong antibody responses are induced in post II sera by either VLP16 formulated with VLP 18 on adjuvant A (group 3) or by the full combo (group 4)

Similar level of antibodies directed against VLP 16 are measured in both groups and no interference is observed.

Antibody Response Against VLP 18

Strong antibody responses are induced in post II sera by either VLP 18 formulated with VLP 16 on adjuvant A (group 3) or by the full combo (group 4).

Similar level of antibodies directed against VLP 18 are measured in both groups (less than 1.5 fold difference) and no interference was observed.

Antibody Response Against VLP 31

Strong antibody responses are induced in post II sera by either VLP31 formulated alone on adjuvant A (group 1) or by the full combo (group 4).

Similar level of antibodies directed against VLP 31 are measured in both groups, therefore no interference is observed.

Antibody Response Against VLP 45

Strong antibody responses are induced in post II by either VLP 45 formulated alone on adjuvant A (group 2) or by the full combo (group 4).

Similar level of antibodies directed against VLP 45 are measured in both groups, thus no interference is observed.

Conclusions

No interference is observed when the four VLPs (VLPs16, 18, 31 & 45) are delivered as a combination.

The invention claimed is:

1. A mixture of VLPs comprising VLPs containing L1 proteins or functional L1 protein derivatives from HPV 16, HPV 18, HPV 31 and HPV 45 genotypes.

2. A mixture of VLPs according to claim 1, comprising a mixture of HPV 16 VLPs, HPV 18 VLPs, HPV 31 VLPs and HPV 45 VLPs, each VLP comprising L1 proteins or functional L1 protein derivatives from only 1 HPV genotype.

3. A mixture of VLPs according to claim 2, wherein the VLPs are L1-only VLPs comprising HPV L1 protein or functional L1 protein derivatives and no other HPV protein.

4. A mixture of VLPs according to claim 1, comprising VLPs consisting essentially only of proteins from HPV 16, HPV 18, HPV 31 and HPV 45.

5. A mixture of VLPs according to claim 1, wherein at least one L1 protein is a truncated L1 protein.

6. A mixture of VLPs according to claim 1, wherein the composition comprises a VLP containing an L1 protein or functional derivative thereof from an additional HPV genotype.

7. A mixture of VLPs according to claim 6, wherein the additional VLP comprises an L1 protein or functional L1 protein derivative selected from one of HPV 33, 52, 53, 58, 35, 56, and 59.

8. A mixture of VLPs according to claim 1, additionally comprising an HPV early antigen or immunologically active fragment thereof selected from E1, E2, E3, E4, E5, E6, E7 or E8.

9. A mixture of VLPs according to claim 1, formulated with an antigen derived from an organism causing a sexually transmitted disease.

10. A mixture of VLPs according to claim 9, wherein the antigen is an HSV antigen or immunologically active fragment thereof.

11. A mixture of VLPs according to claim 9, wherein the antigen is an HIV antigen or immunologically active fragment thereof.

12. A mixture of VLPs according to claim 9, wherein the antigen is a chlamydia antigen or immunologically active fragment thereof.

13. A mixture of VLPs according to claim 1, comprising an HPV L2 protein or fragment thereof.

14. A mixture of VLPs according to claim 1, additionally comprising an adjuvant.

15. A mixture of VLPs according to claim 14, wherein the adjuvant is an aluminium salt.

16. A mixture of VLPs according to claim 15, wherein the aluminium salt is aluminium hydroxide.

17. A mixture of VLPs according to claim 15, additionally comprising 3D-MPL.

18. A mixture of VLPs according to claim 1, wherein the VLPs contain L1 proteins which are not chimaeric.

19. A method of producing the mixture of VLPs of claim 1, the method-comprising combining VLPs containing L1 proteins or functional L1 derivatives from HPV 16, HPV 18, HPV 31 and HPV 45.

* * * * *